US00PP35599P3

(12) United States Plant Patent
Bull

(10) Patent No.: US PP35,599 P3
(45) Date of Patent: Jan. 23, 2024

(54) ***ECHINACEA* PLANT NAMED 'BULLECHIPUR 111'**

(50) Latin Name: *Echinacea purpurea*
Varietal Denomination: BullEchipur 111

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 24 days.

(21) Appl. No.: 17/974,223

(22) Filed: Oct. 26, 2022

(65) Prior Publication Data

US 2023/0189680 P1 Jun. 15, 2023

Related U.S. Application Data

(60) Provisional application No. 63/360,789, filed on Oct. 28, 2021.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ... A01H 5/02; A01H 5/00; A01H 6/14; A01H 6/1448
See application file for complete search history.

(56) References Cited

U.S. PATENT DOCUMENTS

PP26,639 P3 * 4/2016 Ren ..... Plt./428

* cited by examiner

*Primary Examiner* — June Hwu
(74) *Attorney, Agent, or Firm* — The Webb Law Firm

(57) ABSTRACT

A new and distinct variety of *Echinacea* plant having a compact growth habit and large, orange colored blooms.

1 Drawing Sheet

Botanical classification: *Echinacea purpurea.*
Varietal denomination: 'BullEchipur 111'.

BACKGROUND OF THE INVENTION

The present invention comprises a new and distinct cultivar of *Echinacea* plant known by the varietal name 'BullEchipur 111'. The new variety was discovered in August of 2020 in Gönnebek, Germany as the result of a planned breeding program with the purposes of providing *Echinacea* plants with unique flower colors, a compact growth habit, increased branching, and more uniformity when compared to prior *Echinacea* plants. The new variety is the result of a cross between an unpatented *Echinacea purpurea* variety having an internal breeder's reference of "Bul Mix 2019" (female parent) and an unpatented *Echinacea purpurea* variety having an internal breeder's reference of "Bul Mix 2019-21" (male parent) from the breeder's own collection. The new variety was first asexually reproduced via in-vitro tissue culture cuttings in Gönnebek, Germany in September of 2020. The new variety is similar to its parental varieties in botanical classification, but exhibits a more compact growth habit, larger flower size, and different flower color than both of its parental varieties. Further, 'BullEchipur 111' exhibits better branching than its female parent (the female parent has 8-12 branches, the claimed variety has 10-20 branches). Also, 'BullEchipur 111' exhibits smaller leaves and earlier flowering than its male parent (the male parent has 6.0-22.0 cm long and 3.0-7.0 cm wide leaves, the claimed variety has 4.0-20.0 cm long and 1.0-5.0 cm wide leaves).

When 'BullEchipur 111' is compared to *Echinacea purpurea* variety named 'Balsomador' (U.S. Plant Pat. No. 26,639, marketed as "Sombrero® Adobe Orange"), 'BullEchipur 111' is similar to 'Balsomador' in botanical classification and flower color, but 'BullEchipur 111' exhibits a more compact growth habit ('Balsomador' is generally 48.1 cm high) with increased branching ('Balsomador' has approximately 4 main flowering stems) and larger flowers (the inflorescence diameter of 'Balsomador' is approximately 9.3 cm) that distinguish it from the comparison variety. Further, the following characteristics distinguish 'BullEchipur 111' when generally compared to other *Echinacea* varieties known to the breeder:

Orange flower color;
Large flowers;
A compact and uniform growth habit;
High branching;
Fast crop time;
Early flowering; and
Small leaves.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWINGS

The accompanying photographic drawing illustrates the new variety at 22 weeks of age, with the color being as nearly true as is possible with color illustrations of this type:

FIG. 1 shows an entire plant of the new variety.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 19 cm (3 liter) pots under normal field production conditions, and the color readings and measurements were observed outdoors under natural light on 22 week old plants in Gönnebek, Germany Color references are primarily to the 2015 R.H.S. Colour Chart of The Royal Horticultural Society of London, Sixth Edition, except where terms of ordinary significance are used.

PLANT

Time to initiate roots: About 7 days at approximately 19-20° C.

Time to develop roots: About 40-50 days at approximately 18° C.

Time to produce a finished flowering plant from a rooted cutting: About 12-14 weeks in a 19 cm container.

Rooting habit: Exhibits numerous roots that are freely branching and healthy in appearance.

Plant height: From 35.0-50.0 cm, but averages closer to 35.0 cm.

Plant width: 25.0-30.0 cm.

Habit: Upright, compact, and uniform growth with numerous branches.

Disease/pest resistance: Nothing unusual noted to date.

Temperature tolerance: Nothing unusual noted to date.

Drought tolerance: Average.

Branches (flowering stems):

*Number per plant.*—10-20.
*Length.*—20.0-30.0 cm.
*Diameter.*—3.0-10.0 mm.
*Internode length.*—1.0-5.0 cm.
*Angle.*—Upright and outward.
*Strength.*—Strong.
*Texture.*—Pubescence present.
*Color.*—Close to Yellow-Green Group RHS 144A at the bottom, graduating up to 147A at the top.

Foliage:

*Arrangement.*—Single.
*Leaf.*—Length: 4.0-20.0 cm. Width: 1.0-5.0 cm. Shape: Lanceolate. Apex: Acuminate. Base: Attenuate to acute. Margin: Entire. Aspect: Straight to curved. Texture: Upper surface: Rough. Lower surface: Rough. Rugosity: Medium. Color: Young leaves: Upper surface: Close to Green Group RHS 137B. Lower surface: Close to Green Group RHS 137C. Mature leaves: Upper surface: Close to Green Group RHS 137B. Lower surface: Close to Green Group RHS 137C. Petiole: None present. Veins: Venation type: Cross-venulate to longitudinal. Color: Upper surface: Close to Yellow-Green Group RHS 145A. Lower surface: Close to Yellow-Green Group RHS 145B.

INFLORESCENCE

Bud:

*Diameter.*—1.0-3.5 cm.
*Length.*—1.3-2.0 cm.
*Color.*—From Green Group RHS N138B at the young stage up to Greyed-Purple Group RHS 187A just before opening.

Appearance: Elliptic-shaped ray florets and tubular-shaped disc florets.

Natural flowering season: Flowering occurs from July-September in Gönnebek, Germany, beginning approximately 12-14 weeks after planting.

Average number of inflorescences per plant: 10-20.

Average number of inflorescences per branch: 1-3.

Disc and ray floret arrangement: Disc florets are arranged in the middle of the receptacle of the composite, single, freely flowering plant, with ray florets extending outwardly therefrom.

Fragrance: Faint and sweet.

Inflorescence:

*Diameter.*—4.0-8.0 cm.
*Height (depth).*—2.0-3.5 cm.
*Diameter of disc.*—Approximately 11.5 cm.
*Receptacle height.*—1.0 cm.
*Receptacle diameter.*—1.5-3.5 cm.

Ray florets:

*Number per inflorescence.*—18-26.
*Arrangement.*—In two or three whorls.
*Attitude upon emergence from involucre.*—Horizontal.
*Length.*—2.0-5.5 cm.
*Width.*—1.2-2.0 cm.
*Shape.*—Elliptical.
*Apex.*—Obtuse, with indentations of deep depth.
*Base.*—Acute.
*Margin.*—Entire.
*Texture.*—Upper surface: Smooth and glabrous. Lower surface: Rough.
*Color.*—When opening: Upper surface: Close to Orange Group RHS 28A. Lower surface: Close to Red Group RHS 39B. At maturity: Upper surface: Close to Orange-Red Group RHS 34D. Lower surface: Close to Greyed-Red Group RHS 180D. Ground color description: Close to Orange Group RHS 28A.
*Venation.*—Appearance: Parallel. Color: Upper surface: Same color as the florets. Lower surface: Same color as the florets.

Disc florets:

*Number per inflorescence.*—Numerous; too many to quantify.
*Arrangement.*—In the center of receptacle.
*Length.*—8.0-15.0 mm.
*Width.*—1.0-2.0 mm.
*Shape.*—Tubular.
*Apex.*—Pointed.
*Color.*—Immature: Close to Greyed-Purple Group RHS 187A. At maturity: Close to Greyed-Purple Group RHS 187B.
*Paleae.*—Average length: 12.0-15.0 mm. Color: Main color is close to Green Group RHS 138A, with close to Greyed-Purple Group RHS 187B below the tip.

Phyllaries:

*Number per inflorescence.*—40-50.
*Arrangement.*—In three to four whorls.
*Length.*—Approximately 1.0 cm.
*Width.*—2.0-4.0 mm.
*Shape.*—Lanceolate.
*Apex.*—Elongated oval.
*Base.*—Fused.

*Margin.*—Entire.

*Texture.*—Upper surface: Rough. Lower surface: Rough.

*Color.*—Immature: Upper surface: Close to Green Group RHS NN137C. Lower surface: Close to Green Group RHS NN137C. At maturity: Upper surface: Close to Green Group RHS NN137C. Lower surface: Close to Green Group RHS NN137C.

Reproductive organs:

Androecium:

*Presence.*—On disc florets.

*Number* (*per floret*).—One.

*Filament length.*—1.0-2.0 mm.

*Filament color.*—Orange-brown.

*Anther.*—Shape: Oval. Length: 1.0 mm. Color: Orange-brown.

*Pollen.*—Color: Close to Yellow-Orange Group RHS 15B. Amount: Plentiful - too much to quantify.

Gynoecium:

*Presence.*—In disc and ray florets.

*Pistil length.*—1.0-2.0 mm.

*Stigma.*—Shape: Two-parted. Color: Orange-brown.

*Style.*—Length: 1.0-2.0 mm. Color: Orange-brown.

Seeds:

*Overall size.*—1.0-2.0 mm.

I claim:

1. A new and distinct variety of *Echinacea* plant named 'BullEchipur 111', as is herein illustrated and described.

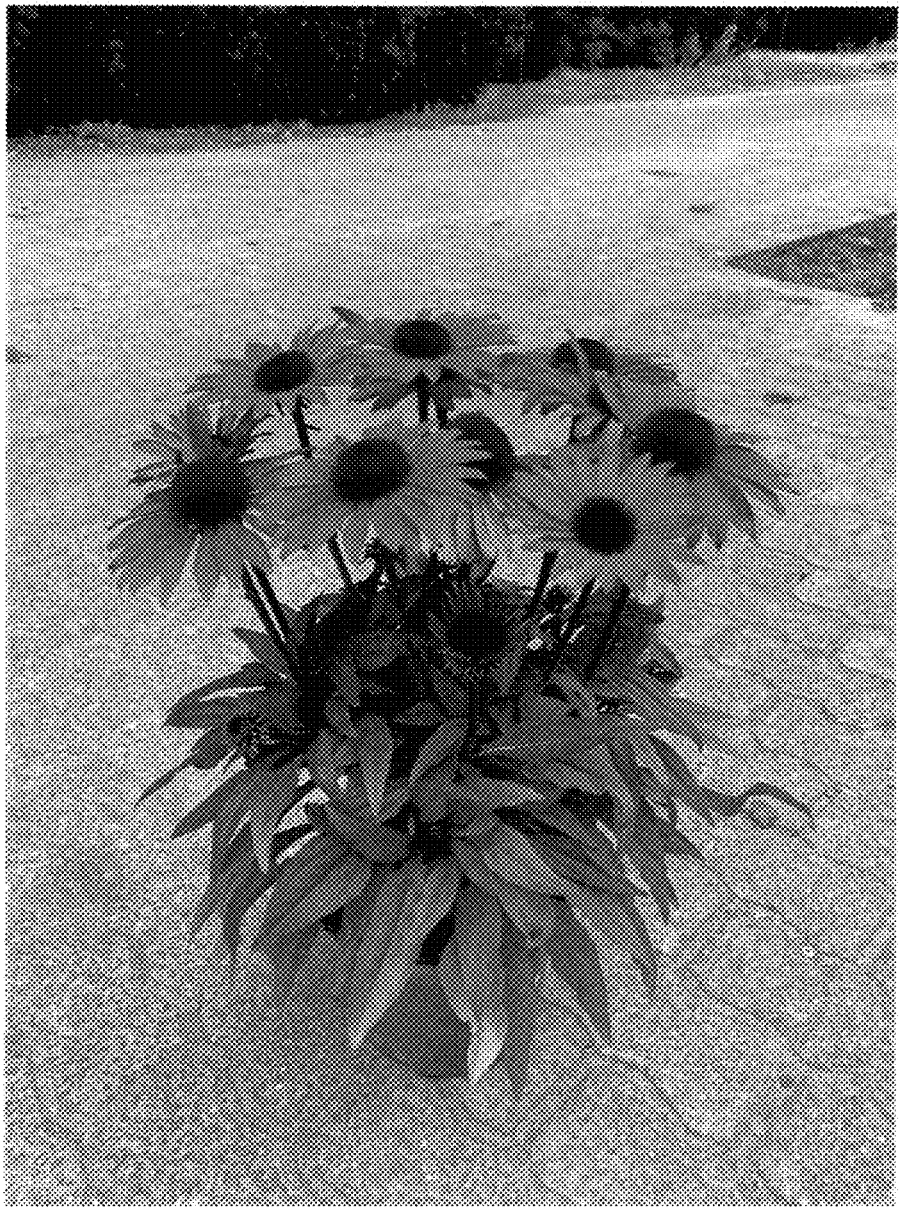

* * * * *